(12) United States Patent
Mitelberg et al.

(10) Patent No.: US 6,613,074 B1
(45) Date of Patent: Sep. 2, 2003

(54) ENDOVASCULAR ANEURYSM EMBOLIZATION DEVICE

(75) Inventors: Vladimir Mitelberg, Aventura, FL (US); Susana Martinez, Coral Gables, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/518,398

(22) Filed: Mar. 3, 2000

Related U.S. Application Data

(60) Provisional application No. 60/123,574, filed on Mar. 10, 1999.

(51) Int. Cl.[7] ................................................ A61F 2/06
(52) U.S. Cl. ...................................... 623/1.11; 606/200
(58) Field of Search ............................... 623/1.11, 1.13; 606/191, 200, 198, 108

(56) References Cited

U.S. PATENT DOCUMENTS

| | | | |
|---|---|---|---|
| 4,517,979 A | | 5/1985 | Pecenka |
| 4,545,367 A | | 10/1985 | Tucci |
| 5,078,726 A | | 1/1992 | Kreamer |
| 5,108,407 A | | 4/1992 | Geremia et al. |
| 5,122,136 A | | 6/1992 | Guglielmi et al. |
| 5,122,154 A | | 6/1992 | Rhodes |
| 5,334,210 A | | 8/1994 | Gianturco |
| 5,382,259 A | | 1/1995 | Phelps et al. |
| 5,383,926 A | | 1/1995 | Lock et al. |
| 5,540,701 A | * | 7/1996 | Sharkey et al. ............. 606/198 |
| 5,562,724 A | | 10/1996 | Vorwerk et al. |
| 5,591,195 A | | 1/1997 | Taheri et al. |
| 5,628,784 A | | 5/1997 | Strecker |
| 5,662,702 A | | 9/1997 | Keranen |
| 5,782,905 A | | 7/1998 | Richter |
| 5,824,043 A | * | 10/1998 | Cottone ..................... 623/1.13 |
| 5,951,599 A | * | 9/1999 | McCrory .................... 606/108 |
| 6,063,111 A | * | 5/2000 | Hieshima et al. .......... 623/1.13 |
| 6,093,199 A | * | 7/2000 | Brown et al. ............... 606/200 |
| 6,165,194 A | * | 12/2000 | Denardo .................... 606/191 |
| 6,214,036 B1 | * | 4/2001 | Letendre et al. ........... 623/1.11 |
| 6,231,597 B1 | * | 5/2001 | Deem et al. ............... 623/1.11 |

FOREIGN PATENT DOCUMENTS

| | | |
|---|---|---|
| WO | WO 99/02092 | 1/1999 |
| WO | WO 99/62432 | 12/1999 |
| WO | WO 99/65397 | 12/1999 |
| WO | WO 00/07524 | 2/2000 |

* cited by examiner

*Primary Examiner*—Bruce Snow
*Assistant Examiner*—Brian E Pellegrino

(57) ABSTRACT

The present invention relates to a medical device for placement at a predetermined location within a vessel of the human body, and more particularly, relates to a collapsible aneurysm embolization device that is delivered through the lumen of a catheter and exits the catheter at a predetermined position within the vessel to thereby embolize a blood vessel defect, such as an aneurysm.

23 Claims, 3 Drawing Sheets

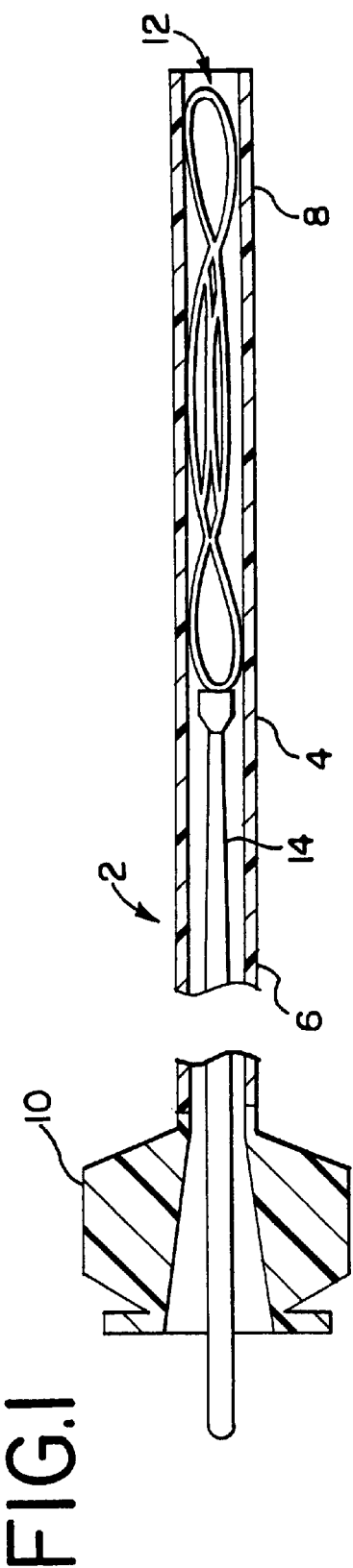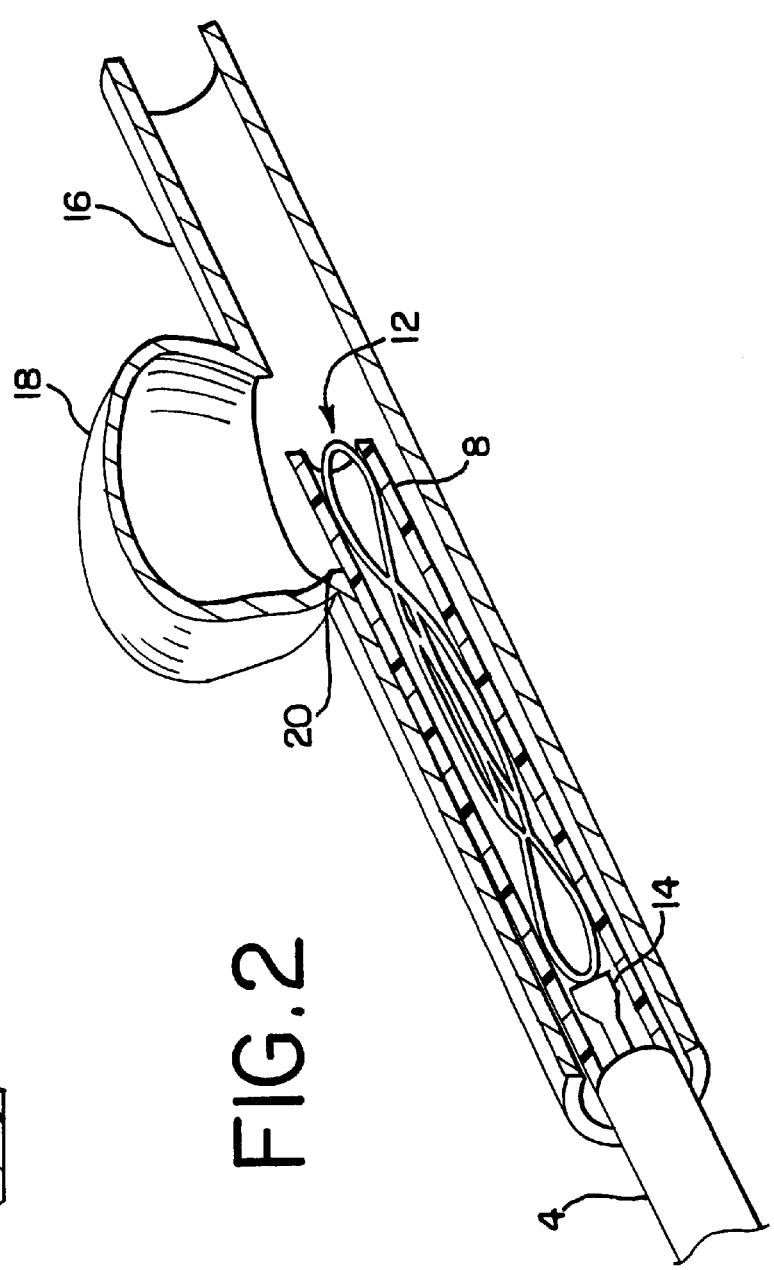

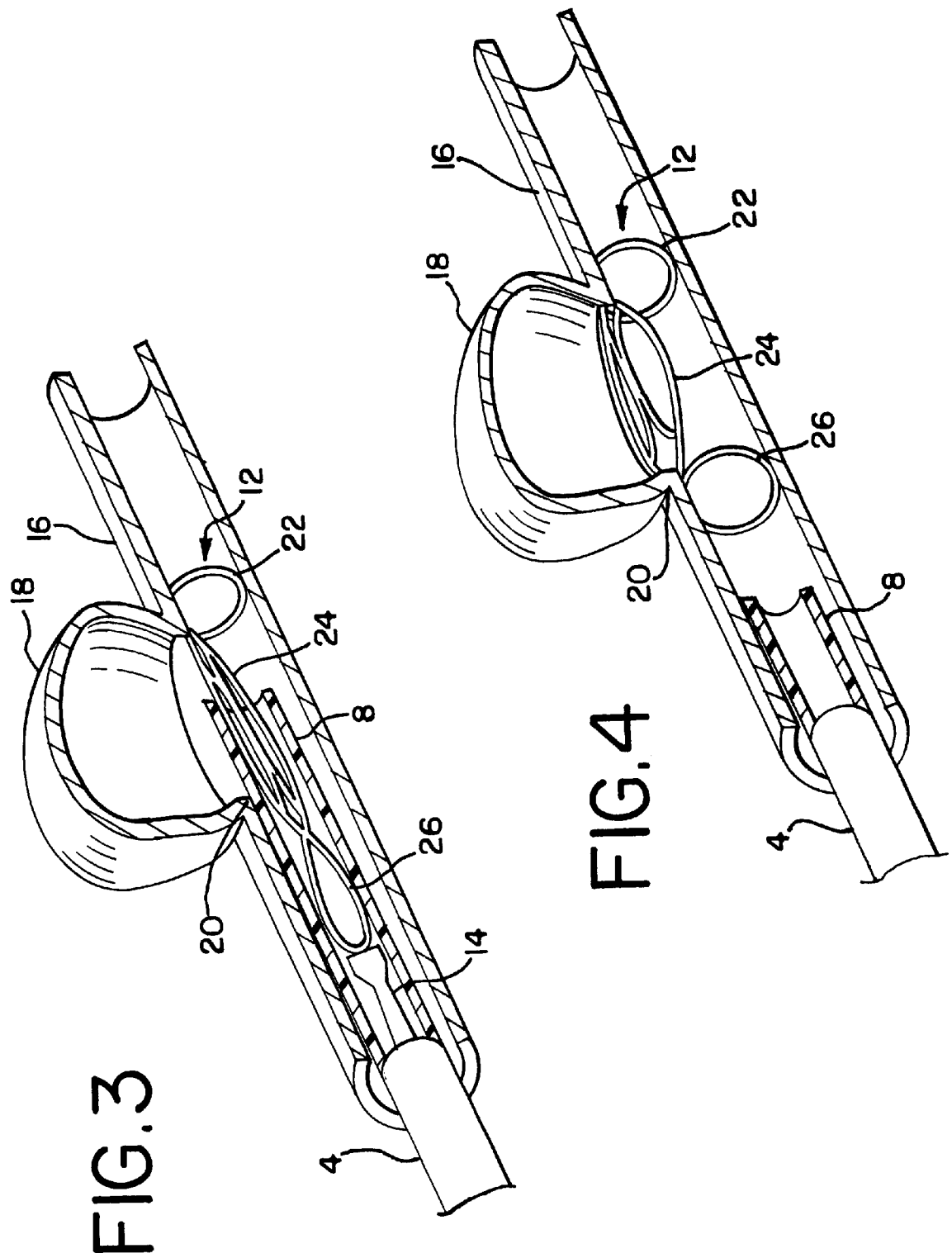

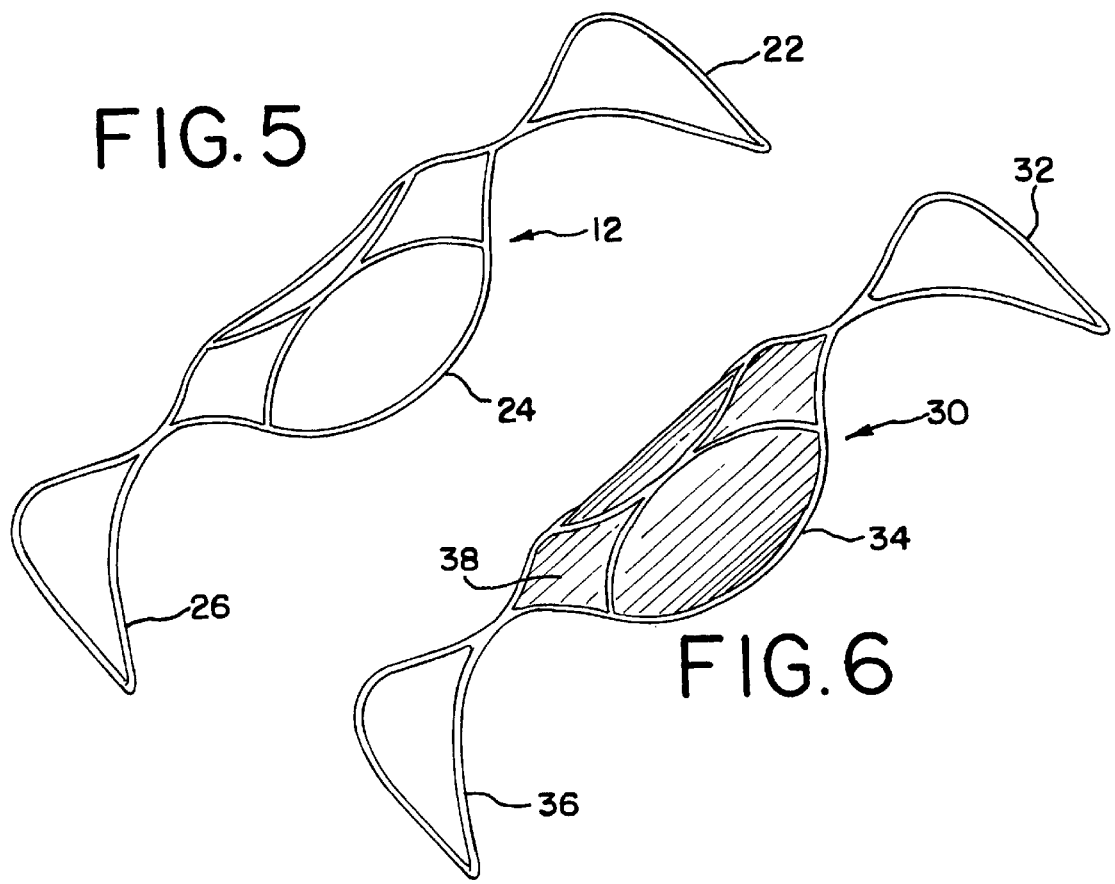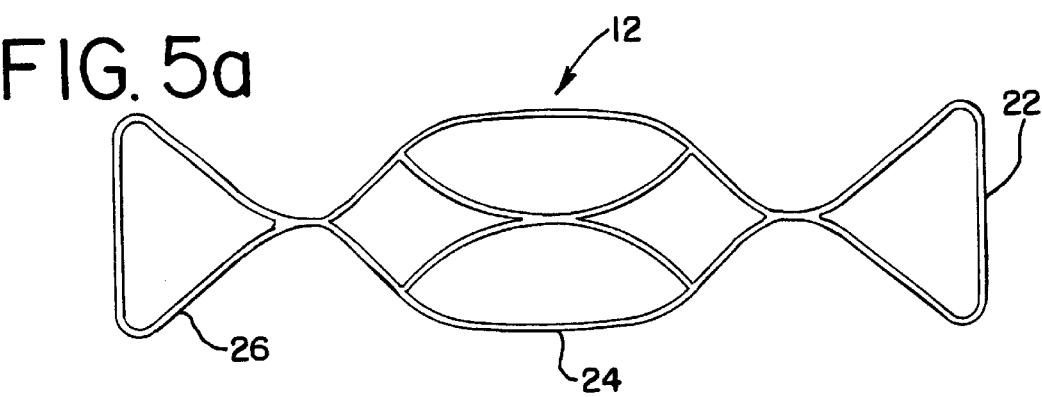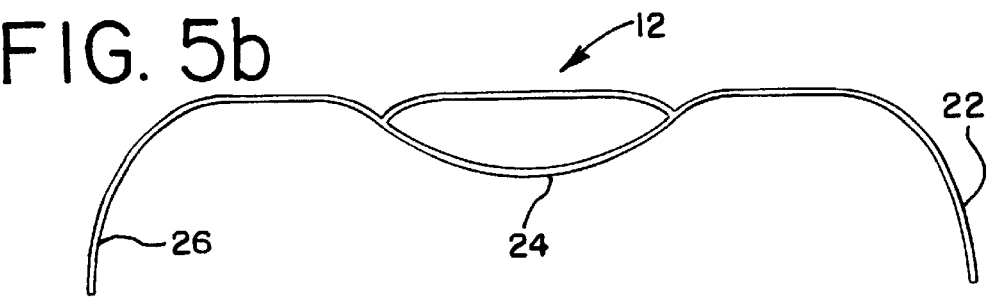

ENDOVASCULAR ANEURYSM EMBOLIZATION DEVICE

CROSS-REFERENCE TO A RELATED APPLICATION

This application claims the benefit of U.S. Provisional Application No. 60/123,574 filed Mar. 10, 1999, the disclosure of which is incorporated herein by reference.

BACKGROUND OF THE INVENTION

1. Field of the Invention

The present invention relates to a medical device for placement at a predetermined location within a vessel of the human body, and more particularly, relates to a collapsible embolization device that is delivered by a catheter at a predetermined position within the vessel to thereby embolize a defect in the blood vessel, such as an aneurysm.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407 to Geremia, et al., entitled, "Method And Apparatus For Placement Of An Embolic Coil" and U.S. Pat. No. 5,122,136 to Guglielmi, et al., entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils at predetermined positions within vessels of the human body in order to treat aneurysms, or alternatively, to occlude the blood vessel at the particular location.

Coils, which are placed in vessels, may take the form of helically wound coils, or alternatively, may be random wound coils, coils wound within other coils or other such coil configurations. Examples of various coil configurations are disclosed in U.S. Pat. No. 5,334,210 to Gianturco, entitled, "Vascular Occlusion Assembly and U.S. Pat. No. 5,382,259 to Phelps, et al., entitled, "Vasoocclusion Coil With Attached Tubular Woven Or Braided Fibrous Coverings." Embolic coils are generally formed of radiopaque material, such as platinum, gold, tungsten or alloys of these metals. Often times several coils are placed at a given location in order to occlude the flow of blood through the vessel by promoting thrombus formation at the particular location.

In the past, embolic coils have been placed within the distal end of the catheter and when the distal end of the catheter is properly positioned the coil may then be pushed out of the end of the catheter, with for example a guidewire, to release the coil at the desired location. This procedure for placement of the embolic coil is conducted under fluoroscopic visualization such that the movement of the coil through the vasculature of the body may be monitored and the coil may be placed in the desired location.

Other embolization devices, such as detachable balloons, are placed in vessels or aneurysms. These balloons usually take the form of an inflatable elastic balloon with a valve assembly for sealing the balloon when a desired inflation is reached. Examples of various detachable balloons are disclosed in U.S. Pat. No. 4,517,979 to Pecenka, entitled, "Detachable Balloon Catheter" and U.S. Pat. No. 4,545,367 to Tucci, entitled, "Detachable Balloon Catheter And Method Of Use." Detachable balloons are generally formed of a flexible polymer and are inflated with a radiopaque solution for visualization under fluoroscopy. Often several balloons are used to fill the aneurysm space. These balloons do not generally conform to the aneurysm space thereby leaving unoccupied space leading to an incomplete aneurysm embolization. Often times a balloon valve may leak thereby causing other balloons to shift position, which may in turn, occlude the parent artery leading to severe complications.

Included in the list of aneurysm embolization devices are stents. Stents have been used to treat some aneurysms, however, most stents are fairly rigid and cannot access tortuous vascular anatomy. A more flexible stent with the ability to access tortuous vessels is disclosed in U.S. patent application Ser. No. 09/052,402 to Hieshima, et al., entitled, "Stent Aneurysm Treatment System and Method," filed Mar. 31, 1998. Since most stents are designed to open a partially blocked vessel, a substantial amount of material is used to support the vessel wall. In treating many aneurysms this additional material is unnecessary and may have deleterious consequences by blocking small vessels or perforators.

SUMMARY OF THE INVENTION

The present invention is directed toward an aneurysm embolization system for use in placing an aneurysm embolization device at a predetermined site within a vessel which includes an elongated, flexible catheter having proximal and distal ends and a through lumen, a push rod and an aneurysm embolization device. The catheter is positioned within the vasculature with the distal end at the neck of an aneurysm. The aneurysm embolization device is collapsed and slidably positioned within the lumen of the catheter. The push rod is slidably positioned in the catheter proximal to the aneurysm embolization device. As the push rod is moved towards the distal end of the catheter the push rod engages the aneurysm embolization device causing it to exit the distal end of the catheter lumen and to expand into position across the neck of the aneurysm to thereby embolize the aneurysm.

In accordance with another aspect of the present invention, the aneurysm embolization device is comprised of a stabilizing member and an occluding member fixedly attached to the stabilizing member. The aneurysm embolization device is formed from a flexible resilient material, which is sufficiently flexible to be passed through tortuous vasculature. The stabilizing member when expanded generally forms a circular loop. The occluding member when expanded generally takes the form of a wire scaffold positioned across the neck of the aneurysm and generally extends around only a portion of the interior circumference of a blood vessel.

In accordance with still another aspect of the present invention, aneurysm embolization device is comprised of a superelastic nickel titanium alloy.

In accordance with still another aspect of the present invention, aneurysm embolization device is comprised of a radiopaque material.

In accordance with still another aspect of the present invention, the stabilizing member of the aneurysm embolization device takes the form of a semicircle.

In accordance with another aspect of the present invention, the aneurysm embolization device is comprised of first and second stabilizing members and an occluding member fixedly attached between the stabilizing members. The aneurysm embolization device is formed from a flexible resilient material, which is sufficiently flexible to be passed through tortuous vasculature. The first and second stabilizing members when expanded generally form a circular loop. The occluding member when expanded generally takes the form of a wire scaffold positioned across the neck of the aneurysm.

In accordance with another aspect of the present invention, the occluding member of the aneurysm embolization device comprises a cover, which is expanded into position across the neck of an aneurysm.

In accordance with another aspect of the present invention, the occluding member cover of the aneurysm embolization device takes the form of a fabric mesh.

In accordance with another aspect of the present invention, the occluding member cover of the aneurysm embolization device takes the form of an expandable foam.

In accordance with another aspect of the present invention, deployment means are utilized within the catheter to advance the generally cylindrical collapsible aneurysm embolization device through the catheter and position the expanded aneurysm embolization device within the vessel across the neck of an aneurysm.

These aspects of the invention and the advantages thereof will be more clearly understood from the following description and drawings of a preferred embodiment of the present invention:

BRIEF DESCRIPTION OF THE DRAWINGS

FIG. 1 is an enlarged, partially sectioned view of the aneurysm embolization system of the present invention;

FIG. 2 is an enlarged partially sectioned view showing the distal end of the catheter in a vessel prior to deployment of the aneurysm embolization device;

FIGS. 3 and 4 illustrate the sequential steps in the expansion of the aneurysm embolization device as it exits the catheter;

FIG. 5 is an isometric view of an aneurysm embolization device according to a preferred embodiment of the present invention;

FIG. 5A is a top view of the aneurysm embolization device of the present invention;

FIG. 5B is a side view of the aneurysm embolization device of the present invention; and, FIG. 6 is an isometric view of an aneurysm embolization device according to a second preferred embodiment of the present invention.

DESCRIPTION OF A PREFERRED EMBODIMENT

FIG. 1 generally illustrates the aneurysm embolization system 2 which is comprised of a catheter 4, having a proximal end 6 and a distal end 8, a hub 10 attached to the proximal end 6 of the catheter 4, and an aneurysm embolization device 12 slidably disposed within the lumen of the distal end 8 of catheter 4. The lumen of the hub 10 is in fluid communication with the lumen of the catheter 4. A push rod 14 is positioned through the lumen of the hub 10 and into the lumen of the catheter 4.

FIGS. 2, 3, and 4 show the sequential steps in deploying the aneurysm embolization device 12. FIG. 2 shows a partially sectioned view of the aneurysm embolization system 2 in a vessel 16. Vessel 16 contains an abnormal defect commonly referred to as an aneurysm 18. The point of origin of aneurysm 18 from the vessel 16 is commonly referred to as the aneurysm neck 20. FIG. 2 also illustrates the distal end 8 of catheter 4 in close proximity to the aneurysm neck 20. Collapsed within the lumen of the distal end 8 of catheter 4 is the aneurysm embolization device 12.

FIG. 3 illustrates push rod 14 moved distally to cause the first stabilizing member 22 to exit the lumen of the distal end 8 of catheter 4 and to expand into a generally circular configuration within vessel 16. As can be appreciated the diameter of the first stabilizing member 22 is sized to fit the diameter of vessel 16. After the first stabilizing member 22 is deployed, catheter 4 is moved proximally within vessel 16 relative to push rod 14. This action causes occluding member 24 to exit the lumen of the distal end 8 of catheter 4 and to expand into position within vessel 16 across the aneurysm neck 20.

FIG. 4 illustrates complete deployment of the aneurysm embolization device 12 within the vessel 16. As shown in FIG. 4 the second stabilizing member 26 that has exited the lumen of the distal end 8 of catheter 4 and expanded into a generally circular configuration within vessel 16. Also shown in FIG. 4 is the expanded scaffold of occluding member 24. Occluding member 24, which is connected to the first stabilizing member 22 distally and the second stabilizing member 26 proximally is positioned across the aneurysm neck 20 to reduce blood flow into aneurysm 18 and promote thrombus formation within aneurysm 18.

FIGS. 5, 5a, and 5b illustrate different views of the enlarged fully expanded aneurysm embolization device 12. The structure of the aneurysm embolization device 12 is comprised of a first stabilizing member 22, an occluding member 24, and a second stabilizing member 26. As shown in FIG. 5, the aneurysm embolization device 12 is preferably produced as a unitary structure. The preferred method of producing a unitary structure is to laser cut the aneurysm embolization device 12 from a tube. Starting with a tube of material, the pattern of the aneurysm embolization device 12 can be input into a computer controlled laser-cutting machine and the pattern is subsequently cut from the tube. In general, tube wall thickness for this manufacturing process usually ranges from about 0.0002 inches to 0.250 inches. As can be appreciated the diameter of the tube corresponds to the diameter of the stabilizing members 22 and 26. In essence, the aneurysm embolization device is a generally cylindrical structure with a substantial portion of the cylinder removed, so as to form a collapsible cylindrical scaffold with stabilizing members.

As can be seen in isometric view of FIG. 5 the occluding member 24 forms an arched framework that generally has the same radius of curvature as the first stabilizing member 22 and second stabilizing member 26 since these elements are cut from the same cylindrical tube. As is apparent using the manufacturing method of laser-cutting, many different modifications of the occluding member 24 pattern can be achieved such as a lattice or mesh pattern, as well as, modifications to the pattern of the stabilizing members 22 and 26 such as semi-circular configurations. In general the openings within the wall of the scaffold are sufficiently small as to restrict the flow of blood into the aneurysm to thereby promote thrombosis of the aneurysm.

The aneurysm embolization device can be formed from many different materials such as metals, polymers and composites. Some of these materials include stainless steel, nylon, polyesters and polycarbonates, but the preferred materials are superelastic materials, such as some nickel titanium alloys. In the preferred embodiment, a formulation of nickel titanium alloy comprising about 51% to 56% nickel and about 44% to 49% titanium is used. To visualize the aneurysm embolization device 12 under fluoroscopy, numerous radiopaque materials such as gold, platinum, or tungsten can be applied using various methods such as electroplating, ion deposition, and coating. The preferred method of making the aneurysm embolization device 12 visible under fluoroscopy is coating with a polymer such as silicone mixed with tantalum powder.

Because the stabilizing members of the aneurysm embolization device anchor in the blood vessel by applying a radial force against the vessel wall, the stabilizing members are typically sized to fit the vessel, with diameters ranging from about 1 mm to 50 mm. As can be appreciated, the width of the stabilizing members typically depend on the size of the vessel that contains the aneurysm, with the range being between about 0.0005 inches and 0.060 inches. In addition to the variability of the stabilizing member to fit a particular aneurysm, so to must the occluding member be sized to fit the aneurysm neck. Typically the length of the occluding member will be slightly larger than the aneurysm neck, with a range of about 1 mm to 100 mm.

FIG. 6 illustrates a second preferred embodiment of the expanded aneurysm embolization device 30. The aneurysm embolization device 30 is comprised of a first stabilizing member 32, an occluding member 34, a second stabilizing member 36 and a cover 38 attached to the framework of occluding member 34. The cover 38 attached to the occluding member 34 is positioned over the neck of an aneurysm. The cover 38 is intended to significantly reduce or block the flow into the aneurysm. Since the cover must collapse with the aneurysm embolization device 30 to fit within the lumen of the catheter it should be constructed of an elastic material. These materials can include polymers such as silicone, polyethers, polyurethanes, polyimides, hydrogels such as, polyvinyl alcohol or polyvinyl pyrrolidone, and other polymers suitable for implantable use. The configuration of the cover 38 can be a fabric mesh made from any of the aforementioned polymers or superelastic metals, as well as, permeable, semi-permeable, non-permeable membranes and expandable foams. Modifications to visualize the cover 38 under fluoroscopy include the bonding of radiopaque Iodine directly to the polymer or incorporation of radiopaque metals such tantalum or tungsten into the polymer. The preferred embodiment incorporates a radiopaque material such as tantalum into a silicone polymer membrane for cover 38. In general, the cover attached to the collapsible cylindrical scaffold restricts blood flow into the aneurysm to thereby promote thrombosis of the aneurysm.

As is apparent, there are numerous modifications of the preferred embodiment described above which will be readily apparent to one skilled in the art, such as many variations and modifications of the aneurysm embolization device including numerous stabilizing member configurations, and occluding member configurations. These modifications would be apparent to those having ordinary skill in the art to which this invention relates and are intended to be within the scope of the claims that follow.

That which is claimed is:

1. An aneurysm embolization system for treating a blood vessel defect comprising:
    a catheter having proximal and distal ends and a lumen extending therethrough;
    a push rod slidably disposed within the lumen of the catheter; and,
    a collapsible aneurysm embolization device comprised of a stabilizing member and an occluding member;
        said stabilizing member comprises a resilient wire which when released takes the form of a generally circular configuration for stabilizing the embolization device within a blood vessel;
        said occluding member comprises a resilient wire scaffold which when released extends around only a portion of the interior circumference of a blood vessel and forms a configuration adapted to extend across an opening of an aneurysm to thereby embolize the aneurysm, said occluding member is attached to the stabilizing member; and,
        said aneurysm embolization device being collapsed and slidably disposed within the lumen at the distal end of the catheter whereby movement of the push rod distally against the aneurysm embolization device causes the aneurysm embolization device to exit the lumen of the catheter and to expand into position within the blood vessel.

2. The aneurysm embolization system as defined in claim 1, wherein the stabilizing member and the occluding member of said aneurysm embolization device are formed of a nickel titanium alloy.

3. The aneurysm embolization system as defined in claim 2, wherein the stabilizing member and the occluding member of said aneurysm embolization device are comprised of radiopaque material.

4. The aneurysm embolization device as defined in claim 1, wherein the occluding member is formed of a mesh capable of producing thrombus in the aneurysm.

5. An aneurysm embolization system for treating a blood vessel defect comprising:
    a catheter having proximal and distal ends and a lumen extending therethrough;
    a push rod slidably disposed within the lumen of the catheter; and,
    a collapsible aneurysm embolization device comprising a first stabilizing member, a second stabilizing member and an occluding member;
        said first stabilizing member comprises a resilient wire which when released takes the form of a generally circular configuration for stabilizing the embolization device within a blood vessel;
        said second stabilizing member comprises a resilient wire which when released takes the form of a generally circular configuration for stabilizing the embolization device within a blood vessel;
        said occluding member comprises a resilient wire scaffold which when released extends around only a portion of the interior circumference of a blood vessel and forms a configuration adapted to extend across the opening of an aneurysm to thereby embolize the aneurysm, said occluding member is attached distally to the first stabilizing member and attached proximally to the second stabilizing member; and,
        said aneurysm embolization device being collapsed and slidably disposed within the lumen of the catheter whereby movement of the push rod distally against the aneurysm embolization device causes the aneurysm embolization device to exit the lumen of the catheter and to expand into position within the blood vessel.

6. The aneurysm embolization system as defined in claim 5, wherein the first and second stabilizing members and the occluding member of said aneurysm embolization device are formed of a nickel titanium alloy.

7. The aneurysm embolization system as defined in claim 6, wherein said aneurysm embolization device, wherein the first and second stabilizing members and the occluding member of said aneurysm embolization device are comprised of radiopaque material.

8. The aneurysm embolization device as defined in claim 5, wherein the occluding member is formed of a mesh capable of producing thrombus in the aneurysm.

9. An aneurysm embolization system for treating a blood vessel defect comprising:

a catheter having proximal and distal ends and a lumen extending therethrough;

a push rod slidably positioned within the lumen of the catheter; and a collapsible aneurysm embolization device comprising a stabilizing member and an occluding member;

said stabilizing member takes the form of a resilient wire which when released forms a generally circular configuration for stabilizing the embolization device within a blood vessel;

said occluding member comprises a wire scaffold having a cover attached to said wire scaffold, said occluding member with said cover when released, extends around only a portion of the interior circumference of a blood vessel and forms a configuration adapted to extend across the neck of an aneurysm, said occluding member is attached to said stabilizing member; and, said aneurysm embolization device being collapsed and slidably disposed within the lumen of the catheter whereby movement of the push rod distally against the aneurysm embolization device causes the aneurysm embolization device to exit the lumen of the catheter and to expand into the blood vessel.

10. The aneurysm embolization system as defined in claim 9, wherein said cover takes the form of a fabric mesh.

11. The aneurysm embolization system as defined in claim 10, wherein said cover takes the form of a permeable membrane.

12. The aneurysm embolization system as defined in claim 11, wherein said cover comprises a radiopaque material.

13. The aneurysm embolization device as defined in claim 11, wherein said cover comprises an expandable foam.

14. An aneurysm embolization system for treating a blood vessel defect comprising:

a catheter having proximal and distal ends and a lumen extending therethrough;

a push rod slidably positioned within the lumen of the catheter; and, a collapsible aneurysm embolization device comprising a first stabilizing member, a second stabilizing member and an occluding member;

said first stabilizing member comprises a resilient wire which when released takes the form of a generally circular configuration for stabilizing the embolization device within a blood vessel;

said second stabilizing member comprises a resilient wire which when released takes the form of a generally circular configuration for stabilizing the embolization device within a blood vessel;

said occluding member comprises a wire scaffold having proximal and distal ends and a cover attached to said wire scaffold, said occluding member with said cover when released, extends around only a portion of the interior circumference of a blood vessel and forms a configuration adapted to extend across the neck of an aneurysm, said occluding member is attached at its distal end to the first stabilizing member and attached at its proximal end to the second stabilizing member; and, said aneurysm embolization device being collapsed and slidably disposed within the lumen of the catheter whereby movement of the push rod distally against the aneurysm embolization device causes the aneurysm embolization device to exit the lumen of the catheter and to expand into the blood vessel.

15. The aneurysm embolization system as defined in claim 14, wherein said cover takes the form of a fabric mesh.

16. The aneurysm embolization system as defined in claim 15, wherein said cover takes the form of a permeable membrane.

17. The aneurysm embolization system as defined in claim 16, wherein said cover comprises a radiopaque material.

18. The aneurysm embolization device as defined in claim 14, wherein said cover comprises an expandable foam.

19. An aneurysm embolization device for treating a blood vessel defect comprising:

a catheter having proximal and distal ends and a lumen extending therethrough;

a collapsible aneurysm embolization device which takes the form of a cylinder with a substantial portion of the cylinder removed which comprises:

a first stabilizing member when released forms a generally circular configuration for stabilizing the embolization device within a blood vessel;

a second stabilizing member when released forms a generally circular configuration for stabilizing the embolization device within a blood vessel; and, an occluding member takes the form of a scaffold having a cover and when released said occluding member with said cover extends around only a portion of the interior circumference of a blood vessel and forms a configuration adapted to extend across an opening of an aneurysm.

20. The aneurysm embolization system as defined in claim 19, wherein said cover takes the form of a fabric mesh.

21. The aneurysm embolization system as defined in claim 20, wherein said cover takes the form of a permeable membrane.

22. The aneurysm embolization system as defined in claim 21, wherein said cover comprises a radiopaque material.

23. The aneurysm embolization device as defined in claim 19, wherein said cover comprises an expandable foam.

* * * * *